United States Patent [19]

Hershman et al.

[11] Patent Number: 4,579,689
[45] Date of Patent: Apr. 1, 1986

[54] OXIDATION WITH COATED CATALYST

[75] Inventors: Arnold Hershman, Frontenac; David E. Gross, Kirkwood; Robert M. Friedman, Creve Coeur, all of Mo.

[73] Assignee: Monsanto Company, St. Louis, Mo.

[21] Appl. No.: 700,169

[22] Filed: Feb. 11, 1985

[51] Int. Cl.$^4$ ............................................... C07F 9/38
[52] U.S. Cl. ............................ 260/502.5 F; 423/437; 502/158; 502/159
[58] Field of Search ................ 260/502.5 F; 423/437, 423/580

[56] References Cited

U.S. PATENT DOCUMENTS

| | | | |
|---|---|---|---|
| 3,907,652 | 9/1975 | Wagenknecht et al. | 260/502.5 F |
| 3,950,402 | 4/1976 | Franz | 260/502.5 F |
| 3,954,848 | 5/1976 | Franz | 260/502.5 F |
| 3,969,398 | 7/1976 | Hershman | 260/502.5 F |
| 4,147,719 | 4/1979 | Franz | 260/502.5 F |
| 4,380,663 | 4/1983 | Roscher et al. | 423/437 |
| 4,486,356 | 12/1984 | Bakel | 260/502.5 F |
| 4,507,250 | 3/1985 | Bakel | 260/502.5 F |

FOREIGN PATENT DOCUMENTS 2049697 12/1980 United Kingdom ......... 260/502.5 F

Primary Examiner—J. E. Evans
Attorney, Agent, or Firm—Frank D. Shearin; Raymond C. Loyer

[57] ABSTRACT

Processes are described wherein formaldehyde or formic acid and similar materials are oxidized to produce carbon dioxide and water by contact with oxygen in the presence of a noble metal catalyst on a carbon support that is protected from poisonous amines by a polymer coating.

10 Claims, No Drawings

OXIDATION WITH COATED CATALYST

The present invention relates to processes for the oxidation of formaldehyde, formic acid or the like by contact with oxygen in the presence of a noble metal catalyst. The invention is particularly related to such processes wherein the noble metal catalyst is coated with polydimethylsiloxane.

It is well known that certain amines are poisonous to noble metal catalysts and when such amines are present together with a noble metal catalyst, the catalyst quickly loses its ability to promote the oxidation reaction whereby formaldehyde and formic acid are oxidized to carbon dioxide and water. In such instances the catalyst is termed "poisoned" as the amines are believed to reside on the reactive sites of the catalyst preventing the promotion of the desired reaction. As a result the rate of reaction quickly declines, and the catalyst must be replaced.

It is also known in the prior art that noble metal catalysts promote the oxidation of formaldehyde or formic acid or the like but when employed in the presence of amines such oxidation reaction is not efficiently catalyzed because of the above-mentioned poisoning. Under suitable conditions formic acid and formaldehyde are known to easily react with amines. It is therefore desirable to remove formaldehyde by oxidation to eliminate contamination or prevent undesired secondary reactions wherein the formaldehyde and formic acid react with the amine to form an undesired by-product. The addition of such catalyst to a mixture containing poisonous amines has been unsatisfactory because the amines poison the catalyst such that its ability to promote the oxidation of formaldehyde is drastically reduced or eliminated.

Protection of the noble metal catalyst by means such as coating it with a protective layer could reduce or eliminate contact of the catalyst with the reactants. To provide contact between reactants and the noble metal catalyst, the coating must allow permeation of the reactants (e.g., formaldehyde, formic acid, and oxygen) inward to the catalyst and the oxidation products (carbon dioxide and water) outward away from the catalyst. Further the rates of permeation must be appropriate to maintain low levels of formaldehyde and formic acid. Of course, the coating must also be impermeable to materials which poison the noble metal catayst. Thus, such coating must be selectively permeable to allow the catalyst to promote the desired reaction while protecting it from poisoning by other materials in the reaction mixture with the catalyst. Finally, the coaing mist withstand degradation in the environment of the reaction and cannot interact with other chemicals in the reaction mixture.

Therefore, finding a suitable coating for the noble metal catalyst which will, at the same time promote the desired oxidation of formaldehyde, formic acid or the like while protecting the noble metal catalyst from poisonious materials, such as amines, has been extremely difficult and few materials found which possess the desired combination of properties.

BRIEF DESCRIPTION OF THE INVENTION

There has now been discovered a selectively permeable catalyst particle comprising a noble metal catalyst on a carbon support coated with a polymer selected from the group consisting of polysiloxanes, polypropylenes, polyvinylfluorides, and 2,6-dimethylpolyphenylene oxides. Because of facile coating techniques, polydimethylsiloxane is preferred. Such catalyst is particularly useful in catalyzing the oxidalion of formaldehyde in a reaction mixture containing amines because these polymers have been found to allow formaldehyde to pass through the polymer film while preventing the passage of amines. One such reaction mixture in which the coated noble metal catalyst of this invention has been found to be extremely useful is the oxidative cleavage of N-phosphonomethyliminodiacetic acid. Such progess is described in U.S. Pat. No. 3,969,398 to Hershman. A co-product of this reaction is formaldehyde. If allowed to remain in the reaction product at high levels, e.g., above about 0.5% by weight, some of the formaldehyde will also be oxidized to formic acid, and the formaldehyde and formic acid will produce an undesirable secondary reaction whereby N-methyl N-phosphonomethylglycine is formed. In corporation of the catalyst of this invention in solutions containing the reaction product containing N-phosphonometylglycine, formaldehyde, and formic acid has been found to effectively prevent by-product formation caused by the reaction of the formic acid, formaldehyde, and N-phosphonomethylglycine. Optimally, the permeation rate of formaldehyde through the polymer coating is sufficient to remove it from the reaction mixture by oxidation so as to maintain such low concentrations in the reaction mixture.

DETAILED DESCRIPTION OF THE INVENTION

The catalyst employed in the process of this invention is a noble metal catalyst, preferably platinum or palladium, on a carbon support as is known in the prior art. Other noble metal catalysts that can be employed on carbon support are rhodium, iridium, and any mixture of noble metals. The noble metal catalyst on a carbon support for use in the present invention is commercially available and such commercial material can be employed directly herein.

The noble metal catalyst on its support is coated with a polymer of this invention, preferably polydimethylsiloxane. A conveniently available form of polydimethylsiloxane is commercially available material sold under the trademarks Sylgard ® by Dow-Corning Inc. or GEXF ® siloxanediol from General Electric Corp. The catalyst on its support is typically coated with the polydimethylsiloxane by dissolving the polymer in a suitable solvent, such as a low molecular weight hydrocarbon, and the noble catalyst on its support is dispersed in the solution to form a slurry. The solvent is then evaporated leaving the catalyst coated with polydimethylsiloxane. The coated catalyst is heated in a vacuum at 60° C. to promote the curing process of the polymer. The coated catalyst may be broken into small particles typically by stirring during the drying process whereby the solvent is removed. There are numerous procedures in the prior art to form coated catalysts and any convenient method may be employed to prepare the catalyst of the present invention. The commercial suppliers of the polymers employed in this invention provide directions for curing those polymers requiring such treatment and such curing processes are readily adapted to provide the degree of curing proper for the catalysts of this invention keeping in mind the environment of intended end use of the coated catalyst.

The coated catalyst is typicaly provided in particulate form having particle sizes ranging from submicron up to about 5 millimeters in diameter. Preferably the coated catalyst particles have a diameter of from about 100 to about 1,000 microns. Small particle size is not preferred because difficulty is experienced in separating the catalyst from the reaction mixture. As long as the coated catalyst is not affected by the reaction conditions, it is conveniently recovered for further use from the reaction mixture.

Loading of the coated catalyst of this invention with supported noble metal is not critical but is maintained in a range which allows for a minimum polymer film thickness that conveniently maintains film continuity over the supported catalyst. For example, in the usual solvent coating method for polydimethylsiloxane, a ratio of 3 parts by weight polymer is dissolved in a suitable solvent. This solution is then combined with 10 parts by weight of catalyst on its support. Typically from about 1 to about 5 parts by weight of polymer may be employed with from about 5 to about 20 parts by weight of carbon supported noble metal.

Catalyst loading on the carbon support is that normally employed in the prior art for oxidation catalyzed reactions and is generally in the range of 0.01 to about 10% noble metal by weight on the carbon support. Higher loadings can be employed but are not cost effective. As is known in the prior art, the preferred range of catalyst loading on the porous support is in the range of 0.05% to about 1%. Such loading has been found to be suitable in the process of the present invention. Many other catalyst supports are known in the art.

It is significant that in some uses, the amount of polymer employed in the production of the coated carbon catalyst is in the range of 30 to 35% by weight of the carbon supported noble metal. Lower ratios of polymer to catalyst can be employed but have been found to be less effective in the prevention of catalyst poisoning by amines, such as N-phosphonomethylglycine.

The temperature employed in carrying out the oxidation process for formaldehyde or formic acid should be sufficient to initiate the reaction and to sustain the reaction once initiated. Temperatures of from about 25° C. to about 150° C. or even higher are usually satisfactory. As those skilled in the art should realize, at lower temperatures the rate of reaction is slower and, therefore, temperatures of at least 50° C. are preferred and even more preferred are temperatures in the range of about 70° C. to about 120° C. It is, of course, realized that at temperatures above about 100° C. that pressure will have to be maintained on the system to maintain a liquid phase.

The manner in which the aqueous solution is contacted with the molecular oxygen-containing gas and catalyst can vary greatly. For example, the solution can be placed in a closed container with some free space containing molecular oxygen and shaken vigorously or agitated by stirring. Alternatively, a tubular reactor can be employed through which the molecular oxygen-containing gas is passed. The tube may be straight or fitted with a frittered diffuser attached thereto. The contacting can also be accomplished in a tubular continuous reactor packed with coated catalyst. Thus, the process of this invention only requires actively contacting the molecular oxygen-containing gas with the aqueous solution of the formaldehyde in the presence of the coated noble metal catalyst of this invention.

The amount of molecular oxygen-containing gas employed can vary over wide ranges. It is, of course, obvious to those skilled in the art that the best yields are produced when at least stoichiometric amounts of oxygen are employed.

By the term "molecular oxygen-containing gas", as employed herein, is meant any gaseous mixture containing molecular oxygen with one or more diluents which are non-reactive with the oxygen or with the reactant or product under the conditions of the reaction. Examples of such gases are air, oxygen, oxygen diluted with helium, argon, nitrogen, or other inert gas and the like or mixtures thereof. It is preferred to employ gases containing 20 or more percent by weight molecular oxygen and even more preferred to employ gases containing 90 or more percent by weight molecular oxygen.

The amount of polymer coated catalyst employed in the process of this invention is not critical and may include a broad range of concentrations. For example, relatively low concentrations are often effective, such as in the range of from about 0.05% to 1% by weight or slightly higher of the reaction medium with the percentages being calculated on the total weight of supported coated platinum or other noble metal and its coating thereon being present. The percentages, of course, should be smaller if based upon the small amount of cataytic metal present on the support and coated with the polymer.

There is thus provided a selectively permeable catalyst which can be used for many applications, such as for rejecting poisons, controlling reactivity, catalytic separations, to control selective reaction of enantiomers and other useful purposes which combine catalysts and polymers.

DESRIPTION OF THE PREFERRED EMBODIMENT

The following examples, illustrating the present invention and methods, are given without any intention that the invention be limited thereto. All percentages are by weight.

EXAMPLE 1

Preparation of Coated Catalyst

To about 10 mL of hexane is added 2.38 gm of polydimethylsiloxane obtained under the tradename Sylgard ® 182 sold by Dow-Corning Inc. and 0.24 gm of curing agent. The mixture was stirred until all of c the Sylgard ® 182 was completely dissolved. The polymer solution was poured over 6 gm of catalyst powder comprising 5% by weight platinum on activated carbon obtained from Engelhard. The mixture was stirred by hand for 5 minutes to obtain a uniform slurry. The solvent was then evaporated by placing the container on a steam bath and introducing dry nitrogen over the surface with constant stirring to break up the catalyst cake. Curing and final drying were effected in a 60° C. vacuum oven for approximately 24 hours and a 20 mesh fraction of the coated polymer obtained.

EXAMPLE 2

To an autoclave, equipped with a mechanical stirrer and temperature measuring and controlling means, is added 2 mL of 37% formaldehyde and 98 mL of deionized water acidified to pH 2 with $H_3PO_4$. uncoated catalyst charge comprising 0.1 gm of 5% palladium on carbon (Engelhard) granular material ground to less than 270 mesh is also added. The mixture was sealed and the reactor heated to 95° C. in about 30 minutes. At this point the pressure was raised and maintained at 30 psig while oxygen gas was allowed to flow through the reactor controlled at 150 sccm. The time of the reaction was measured from when the pressure was achieved and the oxygen allowed to proceed continuously through the reactor thereby purging the carbon dioxide formed in the reaction. The carbon dioxide concentration in the off gas was monitored for the duration of the reaction.

The carbon dioxide in the effluent gas reached a maxim concentration after 15 minutes but quickly reduced after 20 minutes at which time the reaction was terminated. The formaldehyde was found to be completely oxidized.

EXAMPLE 3

Example 2 was repeated with the exception that the catalyst was replaced with the catalyst of Example 1. The carbon dioxide concentration in the effluent reached a maximum after 15 minutes and continued through 27 minutes at which time the reaction was completed. The formaldehyde was found to be completely oxidized. This demonstrates that in a comparable time period complete oxidation of formaldehyde was achieved with a coated catalyst of this invention as compared to the uncoated catalyst.

EXAMPLE 4

The procedure of Example 2 was repeated with the exception that 0.3 gm of disodium salt of ethylenediamine tetraacetic acid is also added along with the formaldehyde. The $CO_2$ concentration in the off-gas reached a peak after 5 minutes and was found to be only 1/5 the amount observed at peak Concentration in Example 2. The reaction continued at a low rate for about 27 minutes as indicated by the amount of $CO_2$ in the off-gas. The formaldehyde was found to be incompletely oxidized indicating that the amine poisoned the uncoated catalyst of this example.

EXAMPLE 5

The procedure of Example 3 was repeated with the exception that 0.3 gm of disodium salt of ethylenediamine tetraacetic acid is also added along with the formaldehyde. The $CO_2$ concentration in the off-gas essentially duplicated that found in Example 3. In contrast to the result found in Example 4 showing catalyst poisoning, this example demonstrated that the coated catalyst was not poisoned by the amine present in the reaction mixture enabling complete oxidation of the formaldehyde.

EXAMPLE 6

A series of reactions were conducted in an autoclave equipped as described in Example 2 above employing a catalyst comprising 0.5% palladium on a porous carbon support (Englehard) to oxidize formaldehyde by contact with oxygen at a temperature in the range of from about 90° C. to about 96° C. The amount of carbon dioxide found in the off-gas as described above was recorded for each reaction to indicate the progress of the oxidation reaction over a period of time. These data are presented in Table I below.

In Example 6a 1 gm of uncoated catalyst was employed with 1.7 mL of 37% aqueous formaldehyde solution and 98 mL of water.

In Example 6b the reaction of Example 6a was repeated with the exception that, in addition, 0.2 gm of iminodiacetic acid were included in the reaction mixture.

In Example 6c 1.4 gm of coated catalyst prepared as described in Example 1 above but with palladium in place of platinum was combined with 1.7 gm of 37% aqueous formaldehyde solution and 98 mL of water.

In Example 6d the procedure of Example 6c was repeated with the exception that 0.2 gm of iminodiacetic acid were also added to the reaction mixture.

In Example 6e the reaction mixture of Example 6d was allowed to stand overnight and then another charge of formaldehyde, 1.7 gm, was added to the reaction mixture. The reaction was conducted for an additional 24 minutes.

TABLE I

| 6a | | 6b | | 6c | | 6d | | 6e | |
|---|---|---|---|---|---|---|---|---|---|
| Time | % $CO_2$ | Time | % $CO_2$ | Time | % $CO_2$ | Time | % $CO_2$ | Time | % $CO_2$ |
| 0 | — | 0 | — | 0 | — | 0 | — | 0 | — |
| 5 | 10.87 | 5 | 1.33 | 5 | 2.42 | 5 | 7.44 | 5 | 4.68 |
| 6 | 12.56 | 6 | 1.48 | 6 | 2.76 | 6 | 8.75 | 6 | 5.54 |
| 7 | 13.85 | 9 | 1.78 | 9 | 3.48 | 9 | 11.32 | 9 | 7.45 |
| 8 | 15.19 | 12 | 1.78 | 12 | 5.77 | 12 | 11.32 | 12 | 7.76 |
| 9 | 15.89 | 15 | 1.78 | 15 | 6.00 | 15 | 10.14 | 15 | 7.83 |
| 10 | 16.24 | 18 | 1.78 | 18 | 6.47 | 18 | 9.16 | 18 | 7.45 |
| 11 | 16.60 | 21 | 1.78 | 21 | 7.96 | 21 | 7.96 | 21 | 7.19 |
| 12 | 16.96 | 24 | 1.78 | 24 | 7.96 | 24 | 6.95 | 24 | 6.47 |
| 13 | 16.96 | 27 | 1.78 | 27 | 7.96 | 27 | 6.00 | | |
| 14 | 17.32 | 30 | 1.78 | 30 | 8.48 | 30 | 5.32 | | |
| 15 | 17.32 | 33 | 1.78 | 33 | 8.48 | 33 | 4.26 | | |
| 16 | 17.32 | 36 | 1.78 | 36 | 7.40 | 36 | 3.67 | | |
| 17 | 17.32 | 39 | 1.78 | 39 | 6.47 | 39 | 3.11 | | |
| 18 | 17.32 | 42 | 1.78 | 42 | 5.54 | 42 | 2.59 | | |
| 19 | 16.96 | 45 | 1.78 | 45 | 4.68 | 45 | 2.25 | | |
| 20 | 16.24 | | | 48 | 3.87 | 48 | 1.78 | | |
| 21 | 14.51 | | | 51 | 3.11 | 51 | 1.63 | | |
| 22 | 12.24 | | | 54 | 2.76 | 54 | 1.33 | | |
| 23 | 10.14 | | | 57 | 2.33 | 57 | 1.26 | | |
| 24 | 7.46 | | | 60 | 2.25 | 60 | 1.19 | | |
| 25 | 6.47 | | | | | 63 | 1.19 | | |

Time is reported in minutes

The data in Table I clearly indicates the effectiveness of the present invention to protect noble metal catalysts from the poisoning effect of amines. A comparison of the results of Examples 6a and 6b illustrates poisoning effect of iminodiacetic acid while the results of Examples 6c and 6d show the protective effect provided by a coating of polydimethylsiloxane while maintaining the ability of the noble metal to catalyze the oxidation of formaldehyde. The results of Example 6e shows the potential for continued use of catalyst of this invention in a suitable reaction medium.

EXAMPLE 7

Into a 300 mL autoclave at 95° C. was added 0.02 moles of formaldehyde and 0.72 gm of coated catalyst. The coated catalyst was prepared by dissolving polydimethylsiloxanediol obtained under the tradename GEXF 382313 from General Electric Corp. in n-pentane to which was added carbon impregnated with 0.5% by weight platinum. The ratio of the above-named polysiloxane to impregnated carbon was 4.5:10. After the coating procedure as in Example 1, the polymer was cross-linked at 60° C. under mild vacuum overnight. Ethylsilicate with dibutyl tin dilaurate catalyst was employed as the cross-linking component. Also added to the autoclave was 0.3 gm of N-phosphonomethylglycine which would act as a poison to the platinum catalyst. While mechanical stirring at 1500 rpm was provided, 150 cc per minute of oxygen was passed through the reaction mixture at 85° C. for 16 hours. The reaction rate was monitored by analysis of the off-gas for $CO_2$. The catalyst was employed in 5 successive oxidation cycles employing fresh charges of formaldehyde in the above procedure while maintaining at least 90% of its original activity as indicated by the percent carbon dioxide in the off-gas stream. This demonstrates reuse of the coated catalyst of this invention even in the presence of N-phosphonomethylglycine, a known poison for noble metal catalysts.

EXAMPLE 8

To a 300 mL autoclave, equipped as described in Example 2, there was added 10 gm of N-phosphonomethyliminodiacetic acid, 100 mL of deionized water, 1 gm of activated carbon commercially available under the tradename Norit A and 0.15 gm of 5% platinum on carbon catalyst which was coated with Sylgard ® 182 at a weight ratio of 5 parts coating to 10 parts platinum on carbon. The mixture was heated to 90° C. and oxygen gas passed through the mixture at a flow rate of 150 scc/min. The pressure was allowed to increase to 2.11 kg/cm$^2$ and the reaction mixture was agitated by stirring at 1500 rpm. The time of reaction is calculated from the time the pressure was allowed to inorease. The amount of $CO_2$ in the off-gas was monitored and the oxidation cleavage reaction endpoint was determined. At the end of the reaction, the contents was filtered leaving the catalyst in the autoclave. The autoclave was then rinsed with 100 mL of deionized water and the rinse combined with the reaction's product. A portion of the reaction mixture was analyzed for formaldehyde and N-phosphonomethylglycine by liquid chromatography. Additional runs as described above were made with the same catalyst by recharging with water and N-phosphonomethyliminodiacetic acid. At recycle No. 4 an additional 0.1 gm of coated catalyst was added. The results of the above-described reactions are summarized in Table II below.

TABLE II

| Recycle No. | Time (min.) | Max. % $CO_2$ in Off-Gas | % Formaldehyde | N—Phosphonomethylglycine (gm) |
|---|---|---|---|---|
| Fresh | 125 | 11.5 | 0.08 | 7 |
| 1 | 125 | 11 | 0.1 | 7.1 |
| 2 | 125 | 9.5 | 0.27 | 6.89 |
| 3 | 125 | 8.5 | 0.28 | 6.4 |
| 4 | 130 | 10 | 0.13 | 6.65 |

As shown by the data in Table II above, the amount of undesired formaldehyde in the reaction product was effectively controlled below 0.5% thereby significantly reducing the possibility of an undesired secondary reaction with N-phosphonomethylglycine to produce N-methyl-N-phosphonomethylglycine. Without the coated catalyst the concentration of formaldehyde would have been expected to be greater than 1% and with the formic acid in solution would have resulted in undesired secondary reaction with N-phosphonomethylglycine.

Other polymers, in addition to polysiloxanes, useful in protecting the noble metal catalysts against poisoning by amines are polypropylene, polyvinylfluoride and 2,6-dimethylpolyphenylene oxide. Such polymers allow permeation of formaldehyde while preventing amines, such as N-phosphonomethylglycine, from reaching the catalyst coated therewith. Continuous coating techniques known in the art may provide suitable catalysts of this invention comprising the above-mentioned polymers and supported noble metal.

As indicated by Example 8 one advantage of the process of this invention is the treatment of a reaction product containing reactive formaldehyde as a by-product in the oxidative cleavage reaction of an N-substituted alpha-amino carboxyl group. As shown by Example 7 the catalyst of this invention can be employed in processes wherein the presence of undesired formaldehyde is removed subsequent to the reaction producing the undesired formaldehyde. Also, materials desirably discarded to waste can be treated to remove undesired formaldehyde. In addition, reaction media tending to have a buildup of formaldehyde from previous processing steps can be freed of formaldehyde and reused by recycle means for further reactions thus realizing more economical operation in manufacturing processes.

The catalyst is also reusable as shown above and can be recovered by various known means for recovering solid catalysts from liquid reaction media.

As indicated by the above examples, the polymers of this invention are capable of protecting the noble metal catalyst from poisoning by a wide variety of amines. Thus, the catalyst of this invention can be employed in a wide variety of reactions wherein it is desired to control the amount of formaldehyde in the reaction medium. Most particularly, the oxidation of tertiary or secondary amines wherein the amine contains at least one N-substituted alpha-amino carboxyl group will normally provide formaldehyde as a by-product. Under conditions of the oxidation reaction, formaldehyde is likewise oxidized to formic acid. Therefore, the elimination of formaldehyde prevents the formation of reactive formic acid. The catalyst of this invention is therefore highly suitable for incorporation into the reaction medium wherein tertiary or secondary amines containing at least one N-substituted alpha-amino carboxyl group is oxidized to a lower amine, i.e., a secondary or primary amine. Likewise, the catalyst of this invention can be employed to remove formaldehyde from amine oxidation reaction products subsequent to the actual oxidation step. In either embodiment the catalyst of this invention is useful in oxidizing formaldehyde thereby eliminating an unwanted by-product from a reaction product containing an amine.

A feature of the catalyst of the present invention is its inherent ability to match the permeation rate of formaldehyde and oxygen with the catalytic reaction rate for the conversion of formaldehyde to carbon dioxide and water. The observed reaction rate reflects both the catalytic reaction rate and the time necessary for the reactants to diffuse to the catalyst and/or for the products of the catalyzed reaction to diffuse outward through the polymer to be released from the coating. Because of the relationship between permeability and reaction rates, the coating on the supported catalyst is desirably very thin to avoid diffusional limitations. As noted above, the thickness of the coating is controlled by the ratio of dissolved polymer and supported catalyst in the coating process.

Although the invention has been described and exemplified by way of specific embodiments, it is not intended to be limited thereto. As will be apparent to those skilled in the art, numerous modifications and variations of these embodiments can be made without departing from the spirit of the invention or the scope of the following claims.

What is claimed is:

1. A process of oxidizing formaldehyde or formic acid in the presence of a poisoning amine which comprises contacting the mixture with oxygen in the presence of a catalyst comprising a noble metal supported on a carbon support coated with a polymer selected from the group consisting of polyusiloxanes, polypropylenes, polyvinylfluorides, and 2,6-dimethylpolyphenylene oxides.

2. A process of claim 1 wherein the polymer is a polysiloxane.

3. A process of claim 2 wherein the polysiloxane is polydimethylsiloxane.

4. A process of claim 1 wherein the formaldehyde or formic acid are produced as by-products in an oxidative cleavage reaction of a tertiary or secondary amine, said amine having at least one N-substituted alpha-amino carboxyl group.

5. A process of claim 3 wherein the noble metal is platinum or palladium.

6. A process of claim 5 wherein the platinum or palladium is present on the carbon support in the range of from about 0.01% to about 10% by weight.

7. A process of claim 6 wherein the catalyst is in particulate form, said particles having a diameter in the range of from about 100 to about 1,000 microns.

8. A process of claim 3 wherein the ratio of noble metal catalyst on a carbon support to polydimethylsiloxane is in the range of from about 3 to about 10, respectively, by weight.

9. A process of claim 4 wherein the tertiary amine is N-phosphonomethyliminodiacetic acid.

10. A process of claim 9 wherein N-phosphonomethylglycine is produced by the oxidative cleavage of the N-phosphonomethyliminodiacetic acid by contact with an oxygen-containing gas in the presence of a catalyst comprising activated carbon.

* * * * *